United States Patent
Lin et al.

(10) Patent No.: US 9,206,101 B2
(45) Date of Patent: Dec. 8, 2015

(54) METHOD FOR HYDROXYLATION OF PHENOL

(71) Applicant: China Petrochemical Development Corporation, Taipei (Taiwan), Taipei (TW)

(72) Inventors: I-Hui Lin, Taipei (TW); Cheng-Fa Hsieh, Taipei (TW); Pin-To Yao, Taipei (TW)

(73) Assignee: China Petrochemical Development Corporation, Taipei (TW)

( * ) Notice: Subject to any disclaimer, the term of this patent is extended or adjusted under 35 U.S.C. 154(b) by 71 days.

(21) Appl. No.: 14/044,108

(22) Filed: Oct. 2, 2013

(65) Prior Publication Data

US 2014/0100392 A1    Apr. 10, 2014

(30) Foreign Application Priority Data

Oct. 4, 2012    (TW) .............. 101136641 A

(51) Int. Cl.
| | |
|---|---|
| *C07C 37/08* | (2006.01) |
| *C07C 37/60* | (2006.01) |
| *B01J 23/75* | (2006.01) |
| *B01J 29/40* | (2006.01) |
| *B01J 29/46* | (2006.01) |
| *B01J 35/00* | (2006.01) |
| *B01J 37/00* | (2006.01) |
| *B01J 37/10* | (2006.01) |

(52) U.S. Cl.
CPC ............ *C07C 37/08* (2013.01); *B01J 23/75* (2013.01); *B01J 29/40* (2013.01); *B01J 29/46* (2013.01); *B01J 35/002* (2013.01); *B01J 37/0018* (2013.01); *B01J 37/10* (2013.01); *C07C 37/60* (2013.01)

(58) Field of Classification Search
CPC .......... C07C 37/08; C07C 37/60; B01J 23/75; B01J 29/40; B01J 29/46; B01J 35/002; B01J 37/0018; B01J 37/10
See application file for complete search history.

(56) References Cited

U.S. PATENT DOCUMENTS

| | | | |
|---|---|---|---|
| 4,396,783 | A | 8/1983 | Esposito et al. |
| 5,399,336 | A | 3/1995 | Guth et al. |

FOREIGN PATENT DOCUMENTS

| | | |
|---|---|---|
| EP | 266825 A1 | 5/1988 |
| GB | 2116974 A | 10/1983 |

OTHER PUBLICATIONS van Bekkum, "Progress in the Use of Zeolites in Organic Synthesis," Chapter 26, Introduction to Zeolite Science and Practice, 3rd Revised Edition, 2007.*
Wang et al., "Cu2+-Exchanged Zeolites as Catalysts for PHenol Hydroxylation with Hydrogen Peroxide," Engery and Fuels, 2004, 18, 470-476.*
Baerlocher, et al., Atlas of Zeolite Framework Types, Sixth Revised Edition, 2007.*

* cited by examiner

*Primary Examiner* — Paul A Zucker
*Assistant Examiner* — Mark Luderer
(74) *Attorney, Agent, or Firm* — Mintz Levin Cohn Ferris Glovsky and Popeo, P.C.; Steven M. Jensen; Richard B. Emmons

(57) ABSTRACT

A method for hydroxylation of phenol is disclosed. The method includes the step of performing a reaction of phenol and hydrogen peroxide to form diphenol in the presence of solid catalyst with zeolite framework, wherein the solid catalyst includes silicon oxide, titanium oxide and cobalt oxide. The solid catalyst used in the preparation of diphenol of the present invention has high conversion rate of diphenol, selectivity of diphenol and higher utilization rate of hydrogen peroxide without using high concentration of hydrogen peroxide.

5 Claims, 1 Drawing Sheet

METHOD FOR HYDROXYLATION OF PHENOL

CROSS-REFRENCES TO RELATED APPLICATIONS

This application claims under 35 U.S.C. §119(a) the benefit of Taiwanese Application No. 101136641, filed Oct. 4, 2012, the entire contents of which is incorporated herein by reference.

BACKGROUND OF THE INVENTION

1. Field of the Invention

This invention relates to a method for hydroxylation of phenol and, more particularly, to a method for catalyzing the hydroxylation of phenol by using solid catalyst containing cobalt.

2. Description of Related Art

In accordance with the variable properties of resorcinol, hydroquinone and pyrocatechol, they are important chemical products which can be applied in various industries, such as electronics, medicine, and chemistry. They are employed in organic synthesis industry such as developer, polymerization inhibitor, skin whitening agent, antioxidant, germicidal agent, rubber additive, electroplating additive, light stabilizer, dye, spice reductant, special ink and the like.

In general, hydroquinone and pyrocatechol are prepared by hydroxylation of phenol using hydrogen peroxide as oxidant with the addition of catalyst to enhance the progression of hydroxylation. At present, zeolite is used as catalyst for the hydroxylation of phenol and it provides the advantage of easily separating catalyst and product after the reaction. The more commonly utilized zeolites are TS-1, ZSM-5, β and Y-type molecular sieve, in which the commercially available TS-1 type molecular sieve has better effects.

U.S. Pat. No. 4,396,783 discloses a titanium-silicon solid catalyst added with a modified metal for use in the hydroxylation of phenol. However, the patent actually used iron, chromium or vanadium to carry out the modification and the yield of diphenol prepared by the hydroxylation of phenol is 8.58% and the highest ratio of hydroquinone and pyrocatechol (H/P) is 0.6.

U.S. Pat. No. 5,399,336 discloses the synthesis of a silicon catalyst (S-1) containing stannum and zirconium, and further discloses performing the hydroxylation of phenol with hydrogen peroxide (70 wt %). The yield of diphenol is 27.5% using S-1 catalyst containing stannum. The yield of diphenol is 28% using S-1 catalyst containing zirconium. Both of these not only have the safety concerns, but also fail to significantly increase the yield of diphenol.

UK Patent No. 2116974 discloses a TS-1 solid catalyst having MFI structure as catalyst for the hydroxylation of phenol. The obtained H/P ratio is 1, and the selectivity of hydrogen peroxide is 73.9%. Likewise, European Patent No. 0266825 discloses a TS-1 solid catalyst containing gallium for carrying out the hydroxylation of phenol. The solid catalysis rate of hydrogen peroxide is 74.7%, and the H/P ratio is 0.79.

From the above, the application of solid catalyst in the conventional techniques for the hydroxylation of phenol still has low H/P ratio of diphenol product and low selectivity of hydrogen peroxide. Besides, the conventional techniques do not employ the solid catalyst containing cobalt in the hydroxylation of phenol.

Therefore, the development of a solid catalyst to increase H/P ratio of the products, selectivity of diphenol, and selectivity of hydrogen peroxide has become an urgent issue to be solved.

SUMMARY OF THE INVENTION

The present invention provides a method for hydroxylation of phenol, comprising the step of performing a reaction of phenol and hydrogen peroxide to form diphenol in the presence of a solvent and a solid catalyst with zeolite framework, wherein the solid catalyst comprises silicon oxide, titanium oxide and cobalt oxide. In one embodiment, the solid catalyst used in the method of the present invention has MEI zeolite framework.

In one preferred embodiment, the solid catalyst used in the method of the present invention is obtained from the hydrothermal reaction of titanium source, silicon source and cobalt source, wherein the molar ratio of titanium from the titanium source to silicon from the silicon source is 0.01 to 0.05. The molar ratio of cobalt from the cobalt source to the silicon from the silicon source is 0.00001 to 0.002.

In the method of the present invention, the reaction is performed at a temperature in a range from 20 to 100° C., preferably from 30 to 80° C., and more preferably from 50 to 70° C. In the method of the present invention, the molar ratio of hydrogen peroxide to phenol is from 0.2 to 1, preferably 0.25 to 0.8, and more preferably 0.33 to 0.6.

In the method of the present invention, the amount of the solid catalyst ranges from 0.5 to 10 wt %, preferably from 1 to 8 wt %, and more preferably from 1.5 to 6.5 wt/%, based on the total weight of phenol and hydrogen peroxide. The solvent may be, but not limited to, alcohol, ketone, nitrile, organic acid or water.

In the present invention, the method for preparing diphenol has high utilization rate of hydrogen peroxide, high conversion rate of phenol, increased product H/P ratio, and increased selectivity of diphenol, and it is suitable for industrial mass production.

DETAILED DESCRIPTION OF THE PREFERRED EMBODIMENTS

Figure 1:
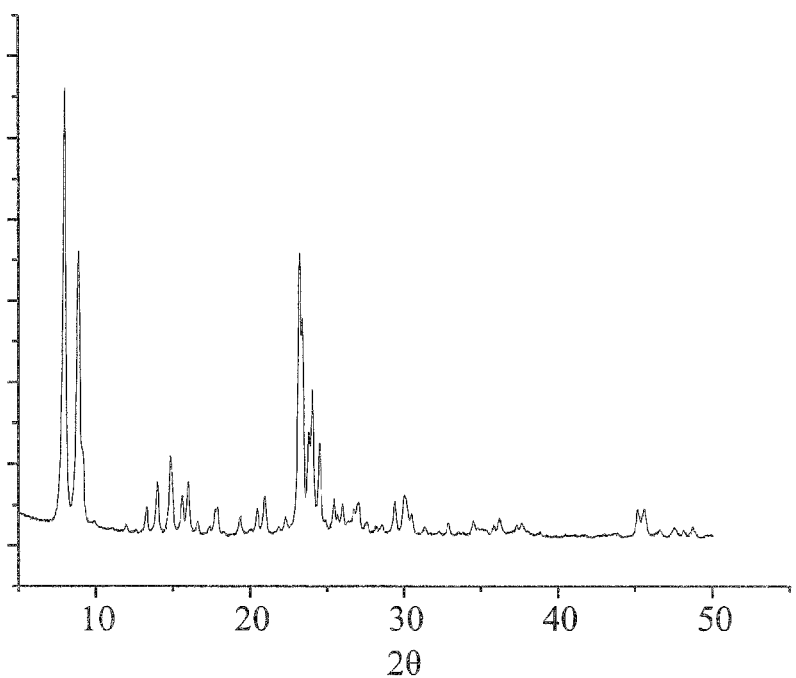
FIG. 1 shows an X-ray pattern of the solid catalyst of according to the first embodiment of the present invention.

The following specific embodiments are used for illustrating the present invention. A person skilled in the art can easily conceive the advantages and effects of the present invention based on the contents disclosed in this specification. The present invention can also be implemented or applied by different specific embodiments, the details of the specification can also be applied based on different perspectives and applications in various modifications and changes without departing from the spirit of the disclosure.

In one preferable example, the solid catalyst of the present invention is prepared by the following preparation, in which silicon source, titanium source and a template reagent are evenly mixed to form a mixed colloidal at 5° C.; and a compound containing cobalt is added to the mixed colloidal for obtaining mixed colloidal containing cobalt. The mixed colloidal containing cobalt is treated hydrothermally. The mixed colloidal containing cobalt treated hydrothermally is sintered to obtain the solid catalyst of the present invention. In the preparation of the solid catalyst of the present invention, the molar ratio of titanium to silicon from the silicon source and the titanium source is 0.01 to 0.05. The molar ratio of cobalt to silicon from the compound containing cobalt and the silicon source is 0.00001 to 0.002. Further, the molar ratio of titanium to silicon and the molar ratio of cobalt to silicon of the solid catalyst can be controlled as 0.01 to 0.05 and as 0.00001 to 0.002 respectively.

In addition, in the preparation of the solid catalyst of the present invention, after forming the mixed colloidal containing cobalt, water or colloidal silica is mixed into the mixed colloidal containing cobalt. Then, the colloidal mixture mixed with water or colloidal silica is subjected to a hydrothermal step.

The silicon source used in the preparation of the solid catalyst of the present invention can be, but not limited to, a silicate ester or a compound represented by formula (I), wherein n is an integer of 1 to 5.

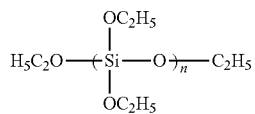

formula (I)

In one embodiment, the used silicon source can be, but not limited to, tetramethyl silicate, tetraethyl silicate, tetrapropyl silicate, tetrabutyl silicate or the combinations thereof. The silicon source may be polyethoxysilane, such as ES-28 (n=1-2), ES-32 (n=3-4) and ES-40 (n=4-5) (Colcoat Corporation).

The titanium source used in the preparation of the solid catalyst of the present invention may be, but not limited to, tetraalkyl titanate. Preferably, the titanium source used in the present invention may be, but not limited to, tetraethyl titanate, tetra-n-propyl titanate, tetra-isopropyl titanate, tetra-n-butyl titanate or the combinations thereof.

The template reagent used in the preparation of the solid catalyst of the present invention may be, but not limited to, tetra-n-propyl ammonium hydroxide, tetra-n-butyl ammonium hydroxide, tetra-n-propyl ammonium bromide, aqueous or alcohol solution of tetra-n-butyl ammonium bromide, wherein the alcohol solution includes an alcohol having 1 to 5 carbon atoms, such as one or more solvent(s) selected from the group consisting of methanol, ethanol, isopropanol, n-butanol and tert-butanol.

The compound containing cobalt used in the preparation of the solid catalyst of the present invention may be, but not limited to, alkoxide, halide or acetate of cobalt. For example, the alkoxide of cobalt may be, but not limited to, methoxyethoxy cobalt; the halide salt of cobalt may be, but not limited to, cobalt chloride, cobalt bromide or its combinations thereof; the cobalt acetate may be, but not limited to, cobalt nitrate, cobalt carbonate, cobalt acetate, acetopyruvate cobalt or a combination thereof.

The following specific embodiments are used for illustrating the present invention. A person skilled in the art can easily understand the other advantages and effects of the present invention by contents disclosed in the present specification. The below embodiments are used to illustrate the present invention. The examples illustrated below should not be taken as a limit to the scope of the invention.

EXAMPLES

Comparative Example 1

The conventional titanium-silicon solid catalyst is prepared as comparative example 1.

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.46 g) were added in the round-bottom flask at 5° C. The mixture was stirred for 1 hour. 44 g of water was added dropwise to the mixture and stirred for 1 hour, followed by stirring for another 1 hour at room temperature. Alcohol was removed at 80° C. for 2 hours. 10.80 g of AS-40 colloidal silica solution was dispersed in 73 g of water to provide a dispersion. The dispersion was then added to the round-bottom flask, and stirred for 1 hour. The alcohol-removed colloidal mixture containing the dispersion was sealed in stainless steel autoclave with Teflon-lining and then treated by a hydrothermal step at 180° C. for 120 hours. After separating the solid from the liquid, the solid was rinsed with water to neutral, then dried at 100° C. and sintered at 550° C. for 8 hours to obtain the catalyst (TS-1A).

Comparative Example 2

The conventional titanium-silicon solid catalyst is prepared as comparative example 2.

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.90 g) were added in the round-bottom flask at 5° C., and stirred for 1 hour. 44 g of water was added dropwise to the mixture and stirred for 1 hour, followed by stifling for another 1 hour at room temperature. Alcohol was removed from the mixture at 80° C. for 2 hours. 10.80 g of AS-40 colloidal silica solution was dispersed in 73 g of water to provide a dispersion. The dispersion was then added to the round-bottom flask, and stirred for 1 hour. The alcohol-removed colloidal mixture containing the dispersion was sealed in stainless steel autoclave with Teflon-lining, and then treated by a hydrothermal step at 180° C. for 120 hours. After separating the solid from the liquid, the solid was rinsed with water to neutral, then dried at 100° C. and sintered at 550° C. for 8 hours to obtain the catalyst (TS-1B).

Preparation of Solid Catalyst of the Present Invention

Embodiment 1

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.46 g) were added in the round-bottom flask at 5° C. and stirred for 1 hour. 0.0626 g of hydrated cobalt nitrate was dissolved in 44.00 g of water to form a cobalt source solution. The cobalt source solution was added dropwise to the round-bottom flask, and stirred for 1 hour, followed by stirring for another 1 hour at room temperature. Alcohol was removed at 80° C. for 2 hours. 10.80 g of AS-40 colloidal silica solution was dispersed in 73 g of water to provide a dispersion. The dispersion was then added to the round-bottom flask, and stirred for 1 hour. The alcohol-removed colloidal mixture containing the dispersion was sealed in stainless steel autoclave with Teflon-lining and then treated by a hydrothermal step at 180° C. for 120 hours. After separating the solid from the liquid, the solid was rinsed with water to neutral, then dried at 100° C. and sintered at 550° C. for 8 hours to obtain the solid catalyst of the present invention (catalyst A), in which the molar ratio of titanium to silicon in the solid catalyst is 0.02, and the molar ratio of cobalt to silicon in the solid catalyst is 0.001.

Embodiment 2

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.46 g) were added in the round-bottom flask at 5° C. and stirred for 1 hour. 0.0313 g of hydrated cobalt nitrate was dissolved in 44.00 g of water to provide a cobalt source solution. The cobalt source solution was added dropwise to the round-bottom flask, and stirred for 1 hour, followed by stifling for another 1 hour at room temperature. Alcohol was removed from the mixture at 80° C. for 2 hours. 10.80 g of AS-40 colloidal silica solution was dispersed in 73 g of water to provide a dispersion. The dispersion was then added to the round-bottom flask, and stirred for 1 hour. The alcohol-removed colloidal mixture containing the dispersion was sealed in stainless steel autoclave with Teflon-lining and then treated by a hydrothermal step at 180° C. for 120 hours. After separating the solid from the liquid, the solid was rinsed with water to neutral, then dried at 100° C. and sintered at 550° C. for 8 hours to obtain the solid catalyst of the present invention (catalyst B), in which the molar ratio of titanium to silicon in the solid catalyst is 0.02, and the molar ratio of cobalt to silicon in the solid catalyst is 0.0005. The X-ray pattern of the catalyst B is shown in FIG. 1. In comparison with Power Diffraction File (PDF) database, the catalyst B has the MFI structure.

Embodiment 3

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.46 g) were added in the round-bottom flask at 5° C. and stirred for 1 hour. 0.0063 g of hydrated cobalt nitrate was dissolved in 44.00 g of water to provide a cobalt source solution. The cobalt source solution was added dropwise to the round-bottom flask, and stirred for 1 hour, followed by stifling for another 1 hour at room temperature. Alcohol was removed from the mixture at 80° C. for 2 hours. 10.80 g of AS-40 colloidal silica solution was dispersed in 73 g of water to provide a dispersion. The dispersion was then added to the round-bottom flask, and stirred for 1 hour. The alcohol-removed colloidal mixture containing the dispersion was sealed in stainless steel autoclave with Teflon-lining and then treated by a hydrothermal step at 180° C. for 120 hours. After separating the solid from the liquid, the solid was rinsed with water to neutral, then dried at 100° C. and sintered at 550° C. for 8 hours to obtain the solid catalyst of the present invention (catalyst C), in which the molar ratio of titanium to silicon in the solid catalyst is 0.02, and the molar ratio of cobalt to silicon in the solid catalyst is 0.0001.

Embodiment 4

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.90 g) were added in the round-bottom flask at 5° C. and stirred for 1 hour. 0.0626 g of hydrated cobalt nitrate was dissolved in 44.00 g of water to provide a cobalt source solution. The cobalt source solution was added dropwise to the round-bottom flask, and stirred for 1 hour, followed by stifling for another 1 hour at room temperature. Alcohol was removed at 80° C. for 2 hours. 10.80 g of AS-40 colloidal silica solution was dispersed in 73 g of water to provide a dispersion. The dispersion was then added to the round-bottom flask, and stirred for 1 hour. The alcohol-removed colloidal mixture containing the dispersion was sealed in stainless steel autoclave with Teflon-lining and then treated by a hydrothermal step at 180° C. for 120 hours. After separating the solid from the liquid, the solid was rinsed with water to neutral, then dried at 100° C. and sintered at 550° C. for 8 hours to obtain the solid catalyst of the present invention (catalyst D), in which the molar ratio of titanium to silicon in the solid catalyst is 0.026, and the molar ratio of cobalt to silicon in the solid catalyst is 0.001.

Embodiment 5

Figure 2:
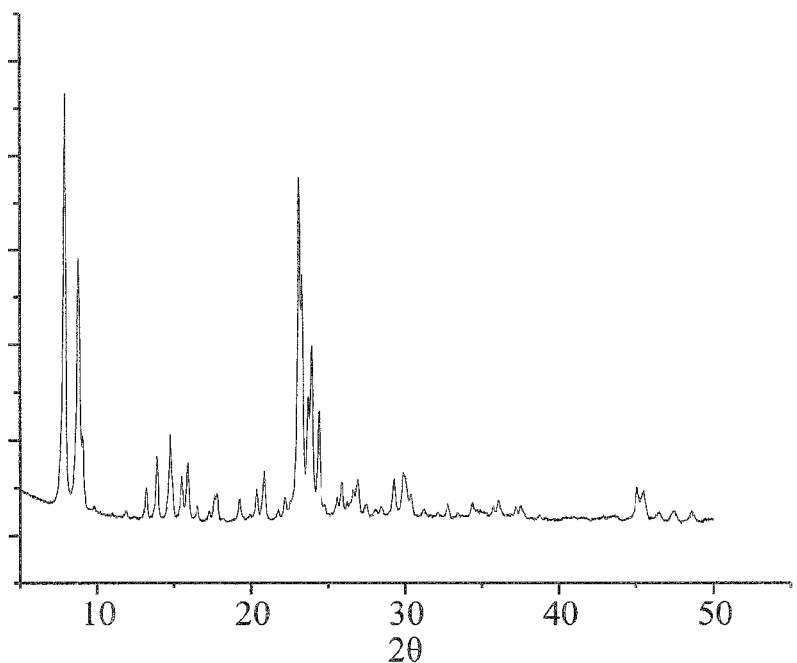
FIG. 2 shows an X-ray pattern of the solid catalyst according to the fifth embodiment of the present invention.

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.90 g) were added in the round-bottom flask at 5° C. and stirred for 1 hour. 0.0313 g of hydrated cobalt nitrate was dissolved in 44.00 g of water to provide a cobalt source solution. The cobalt source solution was added dropwise to the round-bottom flask, and stirred for 1 hour, followed by stifling for another 1 hour at room temperature. Alcohol was removed from the mixture at 80° C. for 2 hours. 10.80 g of AS-40 colloidal silica solution was dispersed in 73 g of water to provide a dispersion. The dispersion was then added to the round-bottom flask, with and stirred for 1 hour. The alcohol-removed colloidal mixture containing the dispersion was sealed in stainless steel autoclave with Teflon-lining and then treated by a hydrothermal step at 180° C. for 120 hours. After separating the solid from the liquid, the solid was rinsed with water to neutral, then dried at 100° C. and sintered at 550° C. for 8 hours to obtain the solid catalyst of the present invention (catalyst E), in which the molar ratio of titanium to silicon in the solid catalyst is 0.026, and the molar ratio of cobalt to silicon in the solid catalyst is 0.0005. The X-ray pattern of the catalyst E is shown in FIG. 2. In comparison with Power Diffraction File (PDF) database, the catalyst E has the MFI structure.

Embodiment 6

A 250 mL round-bottom flask was sealed with nitrogen under vacuum, and tetraethyl silicate (30.00 g), tetra-n-propyl ammonium hydroxide (56.00 g, 20 wt %) and tetra-n-butyl titanate (1.90 g) were added in the round-bottom flask at 5° C. and stirred for 1 hour. 0.0063 g of hydrated cobalt nitrate was added in 44.00 g of water to provide a cobalt source solution. The cobalt source solution was added dropwise to the round-bottom flask, and stirred for 1 hour, followed by stifling for another 1 hour at room temperature. Alcohol was removed from the mixture at 80° C. for 2 hours. 10.80 g of AS-40 colloidal silica solution was dispersed in 73 g of water to provide a dispersion. The dispersion was then added to the round-bottom flask, and stirred for 1 hour. The alcohol-removed colloidal mixture containing the dispersion was sealed in stainless steel autoclave with Teflon-lining and then treated by a hydrothermal step at 180° C. for 120 hours. After separating the solid from the liquid, the solid was rinsed with water to neutral, then dried at 100° C. and sintered at 550° C. for 8 hours to obtain the solid catalyst of the present invention (catalyst F), in which the molar ratio of titanium to silicon in the solid catalyst is 0.026, and the molar ratio of cobalt to silicon in the solid catalyst is 0.0001.

Embodiment 7: Hydroxylation of Phenol

The solid catalysts prepared in Comparative example 1 and Embodiments 1-6 were used to carry out the hydroxylation of phenol in the following procedure.

Phenol (0.178 mole), pure water (1.066 mol) and the catalyst (1.844 g) were added in a 250 mL three-necked bottle under nitrogen and the temperature was raised to 60° C. 35% Hydrogen peroxide (0.089 mole) was introduced in the mixture by pump for 3 hours, followed by standing the reaction for 3 hours. When the temperature was dropped to room temperature, the reaction liquid and the catalyst were separated, and the reaction liquid was analyzed by gas chromatography. The results are shown in Table 1.

TABLE 1

| Solid catalyst | $X_{ph}$ | $S_{diph}$ | $S_{BQ}$ | $X_{H2O2}$ | $S_{H2O2}$ | H/P ratio |
|---|---|---|---|---|---|---|
| TS-1 A | 43.47 | 86.62 | 0.13 | 100.00 | 75.51 | 2.1 |
| catalyst A | 41.09 | 92.27 | 3.04 | 100.00 | 75.61 | 3.0 |
| catalyst B | 44.79 | 87.83 | 4.96 | 100.00 | 78.32 | 2.5 |
| catalyst C | 43.31 | 95.94 | 2.16 | 99.95 | 82.79 | 2.2 |
| catalyst D | 46.99 | 88.72 | 8.93 | 100.00 | 83.04 | 2.9 |
| catalyst E | 48.28 | 95.77 | 3.39 | 100.00 | 92.13 | 2.4 |
| catalyst F | 43.31 | 90.49 | 7.66 | 99.97 | 78.32 | 2.7 |

$X_{ph}$ = conversion rate of phenol = moles of consumed phenol/moles of introduced phenol × 100%;
$S_{diph}$ = selectivity of diphenol = (moles of generated hydroquinone + moles of generated pyrocatechol)/moles of consumed phenol × 100%;
$S_{BQ}$ = selectivity of benzoquinone = moles of generated benzoquinone/moles of consumed phenol × 100%
$X_{H2O2}$ = conversion rate of hydrogen peroxide = moles of consumed hydrogen peroxide/moles of introduced hydrogen peroxide × 100%
$S_{H2O2}$ = selectivity of hydrogen peroxide = moles of generated diphenol/moles of consumed hydrogen peroxide × 100%
H/P ratio = hydroquinone/pyrocatechol ratio = moles of generated hydroquinone/moles of generated pyrocatechol Embodiment 8: Hydroxylation of Phenol The solid catalysts (with the same molar ratio of titanium to silicon) prepared in Comparative example 2 and Embodiment 5 were used to carry out the hydroxylation of phenol at different temperatures in the following procedure.

Phenol (0.178 mole), pure water (1.066 mol) and the catalyst (1.844 g) were added in a 250 mL three-necked bottle under nitrogen and at 55° C., 65° C. and 70° C., respectively. 35% hydrogen peroxide (0.089 mole) were introduced in the mixture by pump for 3 hours, followed by standing the reaction for 3 hours. When the temperature was dropped to room temperature, the reaction liquid and the catalyst were separated, and the reaction liquid was analyzed by gas chromatography. The results are shown in Table 2.

TABLE 2

| solid catalyst | reaction temperature | $X_{ph}$ | $S_{diph}$ | $S_{BQ}$ | $X_{H2O2}$ | $S_{H2O2}$ | H/P ratio |
|---|---|---|---|---|---|---|---|
| TS-1B | 55° C. | 36.24 | 81.18 | 13.37 | 100.00 | 59.08 | 2.5 |
| TS-1B | 65° C. | 40.48 | 91.95 | 5.77 | 100.00 | 74.35 | 2.1 |
| TS-1B | 70° C. | 41.73 | 90.63 | 4.50 | 99.95 | 75.43 | 2.0 |
| catalyst E | 55° C. | 37.83 | 87.67 | 7.69 | 100.00 | 66.12 | 3.4 |
| catalyst E | 65° C. | 47.23 | 93.84 | 2.13 | 100.00 | 88.52 | 2.7 |
| catalyst E | 70° C. | 42.81 | 92.99 | 3.47 | 98.66 | 80.33 | 2.0 |

As shown in the above embodiments, the solid catalyst of the present invention used in the hydroxylation of phenol attains high conversion rate of phenol without the use of high concentration hydrogen peroxide, and further enhances the selectivity of diphenol and H/P ratio of the product. The solid catalyst containing cobalt of the present invention not only reduces the safety concerns of using high concentration hydrogen peroxide, but also has a wider range of active temperature and enhances production efficiency.

The above embodiments are only used to illustrate the principles and effects of the present invention, and should not be construed as to limit the present invention. The above embodiments can be modified and altered by those skilled in the art, without departing from the spirit and scope of the present invention. Therefore, the protection scope of the present invention is defined in the following appended claims.

What is claimed is:

1. A method for hydroxylation of phenol, comprising:
performing a reaction of phenol and hydrogen peroxide to form diphenol in the presence of a solvent and a solid catalyst,
wherein the solid catalyst has MFI zeolite framework, and is obtained from a hydrothermal reaction of titanium source, silicon source and cobalt source, wherein a molar ratio of titanium from the titanium source to silicon from the silicon source is 0.01 to 0.05, and molar ratio of cobalt from the cobalt source to the silicon from the silicon source is 0.00001 to 0.002.

2. The method of claim 1, wherein a molar ratio of hydrogen peroxide to phenol is 0.2 to 1.

3. The method of claim 1, wherein an amount of the solid catalyst is 0.5% to 10% of a total weight of phenol and hydrogen peroxide.

4. The method of claim 1, wherein the reaction is performed at a temperature in a range from 20° C. to 100° C.

5. The method of claim 1, wherein the solvent is one or more selected from the group consisting of alcohol, ketone, nitrile, organic acid and water.

* * * * *